United States Patent [19]

Meilland

[11] Patent Number: Plant 6,164

[45] Date of Patent: May 3, 1988

[54] ROSE PLANT—MEISPOLA VARIETY

[75] Inventor: Marie-Louise Meilland, Antibes, France

[73] Assignee: The Conard-Pyle Company, West Grove, Pa.

[21] Appl. No.: 833,613

[22] Filed: Feb. 27, 1986

[51] Int. Cl.[4] ..... A01H 5/00

[52] U.S. Cl. ..... Plt./14

[58] Field of Search ..... Plt./14

*Primary Examiner*—Robert E. Bagwill

*Attorney, Agent, or Firm*—Burns, Doane, Swecker & Mathis

[57] ABSTRACT

A new and distinct variety of Hybrid Tea rose plant is provided which forms distinctive elegant double pure white blossoms having a delicate fragrance and a long vase life. The plant exhibits a vigorous growth habit and is well suited for cut flower production under greenhouse conditions. Good resistance to fungal diseases is manifest.

1 Drawing Sheet

SUMMARY OF THE INVENTION

The new variety of Hybrid Tea rose plant was created by artificial pollination wherein two parents were crossed which previously had been studied in the hope that they would contribute the desired characteristics. The female parent (i.e., the seed parent) of the new variety was an unnamed seedling. The male parent (i.e., the pollen parent) was produced by crossing the Esther O'Farim variety (U.S. Plant Pat. No. 3,229) with pollen from another unnamed seedling formed by crossing the Super Star variety (U.S. Plant Pat. No. 1,969) by pollen derived from the Flirt variety (U.S. Plant Pat. No. 1,122). The parentage of the new variety can be summarized as follows:

[Unnamed seedling]×[Esther O'Farim'(Super Star×Flirt)].

The seeds resulting from the above pollination were sown in a greenhouse and 8 plantlets were obtained which were physically and biologically different from each other. Selective study resulted in the identification of a single plant of the new variety.

It was found that the new variety of Hybrid Tea rose plant of the present invention possesses the following combination of characteristics:

(a) forms elegant double pure white blossoms having a distinctive delicate fragrance and a long vase life;
(b) is particulary well suited for growing under greenhouse conditions,
(c) exhibits a vigorous group habit, and
(d) exhibits good resistance to fungal diseases.

The new variety well meets the needs of the cut flower industry since the plant is strong and vigorous and grows very well under greenhouse conditions.

The new variety has been found to undergo asexual propagation by a number of routes, including budding, winter bench grafting, etc. The characteristics of the new variety have been found to be strictly transmissible by such asexual propagation from one generation to another.

The new variety has been named the Meispola variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety were observed during February while grafted on *Rosa indica* understock and growing in a greenhouse at Cap d'Antibes, France.

Figures 1, 2, 3, 4, 5, 6, 7, 8, 9, 10, 11, 12, 13, 14, 15, 16:
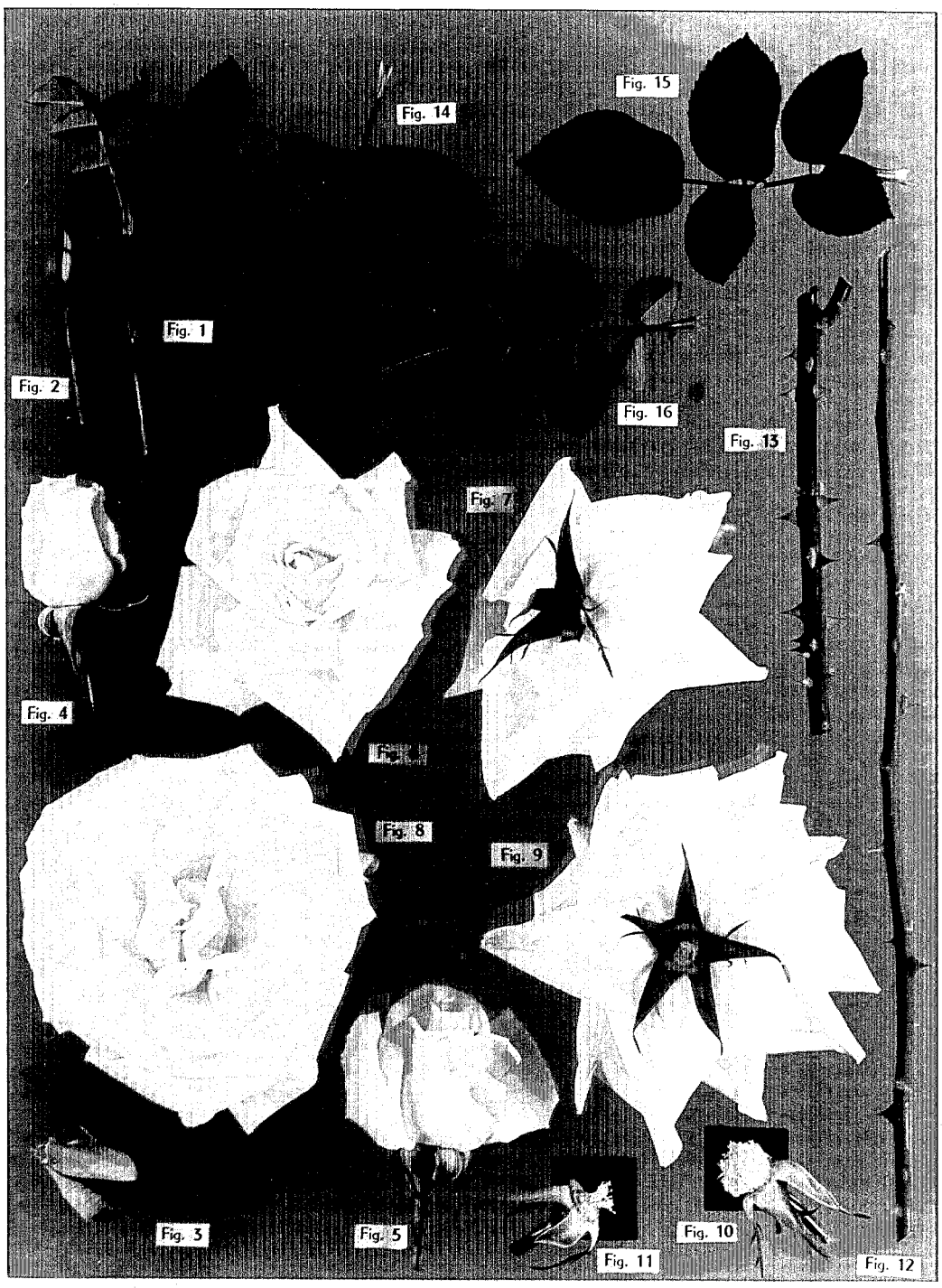
FIG. 1 illustrates a specimen of a young shoot.
FIG. 2 illustrates a specimen of a floral bud before the opening of the sepals.
FIG. 3 illustrates a specimen of a floral bud at the opening of the sepals.

FIG. ∝ illustrates a specimen of a floral bud at the opening of the petals;

FIG. 5 illustrates a specimen of a flower in the course of opening;

FIG. 6 illustrates a specimen of a fully open flower—plan view—obverse;

FIG. 7 illustrates a specimen of a fully open flower—plan view—reverse;

FIG. 8 illustrates a specimen of a fully open flower immediately prior to petal drop—plan view—obverse;

FIG. 9 illustrates a specimen of a fully open flower immediately prior to petal drop—plan view—reverse;

FIG. 10 illustrates a specimen of a floral receptacle showing the arrangement of the stamens and pistils;

FIG. 11 illustrates a specimen of a floral receptacle showing the arrangement of the pistils (stamens removed):

FIG. 12 illustrates a specimen of a flowering stem;

FIG. 13 illustrates a specimen of a main branch;

FIG. 14 illustrates a specimen of a leaf with three leaflets—upper surface;

FIG. 15 illustrates a specimen of a leaf with five leaflets—upper surface; and FIG. 16 illustrates a specimen of a leaf with seven leaflets—upper surface.

DETAILED DESCRIPTION

The chart used in the identification of the colors is that of The Royal Horticultural Society (R.H.S. Colour Chart). The description is based on observations made during February while grafted on *Rosa indica* understock and growing in a greenhouse at Cap d'Antibes, France.

Class: Hybrid Tea.

Plant:

*Height.*—Plants which were pruned to a height of 85 cm. produced floral stems having a length of approximately 40 to 70 cm.

*Habit.*—Upright.

Branches:

*Color.*—Young stems: Yellow-Green Group 146B. Adult wood: Yellow-Green Group 146A.

Leaves:

*Petioles.*—Upper surface: noticeable veination, reddish-brown on young foliage. Under surface: medium green.

*Leaflets.*—Number: 3, 5, and 7 (most often).

*Shape.*—Elliptic.

*Serration.*—Simple and regular.

*General appearance.*—Ample and dense.

*Color (young foliage).*—Upper surface: reddish-brown with a light green central vein. Under surface: reddish-brown.

*Color (adult foliage).*—Upper surface: Green Group 136A. Under surface.—Yellow-Green Group 147B.

Inflorescence:

*Number of flowers.*—Generally one per stem.

*Peduncle.*—Straight, rigid, and smooth.

*Buds.*—Shape: conical at the opening of the sepals and thereafter long. Length: approximately 4.5 cm. Color upon opening: upper surface: pure white, White Group 155A. under surface: pure white, White Group 155A.

*Flower.*—Shape: initially long with a high center changing to the configuration of a deep cup. Diameter: approximately 16.5 cm. on average. Color (when opening begins): upper surface: pure white, White Group 155A. under surface: pure white, White Group 155A. Color (when partially open): upper surface: pure white, White Group 155A. under surface: pure white, White Group 155A. Color (at end of opening): upper surface: pure white, White Group 155A. under surface: pure white, White Group 155A. Fragrance: delicate and attractive. Lasting quality: long. Petal number: approximately 35 on average. Petal form: round with a wide margin, cuneiform base, the outside petals tend to longer than those at the center. Stamen number: approximately 91 on average. Anthers: yellow. Pistils: approximately 72 on average.

Development:

*Disease resistance.*—Exhibits good resistance to major fungal diseases which commonly attack roses.

I claim:

1. A new and distinct variety of Hybrid Tea rose plant characterized by the following combination of characteristics:

(a) forms elegant double pure white blossoms having a distinctive delicate fragrance and a long vase life, (b) is particularly well suited for growing under greenhouse conditions, (c) exhibits a vigorous growth habit, and (d) exhibits good resistance to fungal diseases;

substantially as herein shown and described.

* * * * *